United States Patent [19]

Mandt et al.

[11] 4,381,314

[45] Apr. 26, 1983

[54] CONTACT LENS DISINFECTING AND PRESERVING SOLUTION

[75] Inventors: Lawrence D. Mandt, Fairport; Thomas M. Riedhammer; Francis X. Smith, both of Rochester, all of N.Y.

[73] Assignee: Bausch & Lomb Incorporated, Rochester, N.Y.

[21] Appl. No.: 208,919

[22] Filed: Nov. 21, 1980

[51] Int. Cl.$^3$ ..................... A61K 31/11; A01N 35/00
[52] U.S. Cl. .................................................. 424/333
[58] Field of Search ......................................... 424/333

[56] References Cited

U.S. PATENT DOCUMENTS

| | | | |
|---|---|---|---|
| 3,016,328 | 1/1962 | Pepper et al. | 424/333 |
| 3,697,222 | 10/1972 | Sierra | 424/333 |
| 3,888,782 | 6/1975 | Boghosian et al. | 424/326 |
| 3,912,450 | 10/1975 | Boucher | 424/333 |
| 3,968,248 | 7/1976 | Boucher | 424/333 |
| 3,968,250 | 7/1976 | Boucher | 424/333 |
| 4,093,744 | 6/1978 | Winicov et al. | 424/333 |

FOREIGN PATENT DOCUMENTS 841345 7/1960 United Kingdom ................ 424/333

OTHER PUBLICATIONS

Contact Lenses, Robert H. Hales, The Williams & Wilkins Co., Baltimore, Md. (1978)–p. 33.
Amer J. Hosp. Pharm., 31:546–547 (1974)–RMG, Boucher.
J. Appl. Bact., 37, 83–92 (1974)–Thomas et al.
Chem. Abst., 91:78878(r) (1979)–Laier et al.

Primary Examiner—Douglas W. Robinson
Attorney, Agent, or Firm—Robert M. Phipps

[57] ABSTRACT

A disinfecting and/or preserving solution for contact lenses is disclosed. The solution is an aqueous solution containing 0.00001 to 0.1 weight percent of 1,5-pentanedial, optionally together with up to 0.004 weight percent of thimerosal or other enhancers and optional buffers and the like.

4 Claims, No Drawings

CONTACT LENS DISINFECTING AND PRESERVING SOLUTION

BACKGROUND

1. Field of the Invention

This invention relates to the use of 1,5-pentanedial as the active antimicrobial agent in disinfecting and/or preserving solutions for contact lenses.

2. Description of the Prior Art

This invention relates to disinfecting contact lenses, particularly soft contact lenses. When the term "soft contact lenses" is used herein, it is generally referring to those contact lenses which readily flex under small amounts of force and return to their original shape when released from that force. Typically, soft contact lenses are formulated from poly(hydroxyethyl methacrylate) which has been, in the preferred formulation, crosslinked with ethylene glycol dimethacrylate. For convenience, this polymer is generally known as PHEMA. Soft contact lenses are also made from silicone polymers typically crosslinked with dimethyl polysiloxane. As is known in the art, conventional hard lenses usually consist of poly(methylmethacrylate) crosslinked with ethylene glycol dimethacrylate.

Hard contact lenses do not absorb appreciable amounts of water as do some soft contact lenses and thus the use of harsher disinfecting and cleaning agents does not create a problem in the hard contact lenses cleaning area. However, many hard lens disinfecting and preserving solutions contain benzalkonium chloride or chlorobutanol which may render the treated lenses hydrophobic, may not be stable in solution or lack compatibility with certain types of hard lenses, e.g., high silicone content. As is generally known the users of soft contact lenses are warned against using solutions made for hard contact lenses since the materials in the solutions, as mentioned, may be absorbed or even concentrated by the soft contact lenses and may seriously damage the soft contact lenses or the eye of the user.

U.S. Pat. No. 3,016,328, R. E. Pepper et al, discloses dialdehyde alcoholic sporicidal compositions containing a saturated dialdehyde, e.g., glutaraldehyde, an alkanol and an alkalinating agent. Also disclosed are aqueous sporicidal compositions containing a dialdehyde (0.25 to 4%) and an alkalinating agent, the solution having a pH of 7.4 or more. Medical, surgical and optical applications are suggested.

U.S. Pat. No. 3,697,222, G. Sierra, discloses the use of an aqueous acid glutaraldehyde solution at temperatures above 45° C. to sterilize an object. The sterilizing action is enhanced by the use of ultrasonic energy. Sterilization also may be achieved by using ultrasonic energy and aqueous alkaline glutaraldehyde solutions, the preferred temperature being 55° to 65° C. Sierra teaches the aqueous glutaraldehyde concentration can be up to 7.5% and preferably 1 to 2%.

U.S. Pat. No. 3,912,450 and U.S. Pat. No. 3,968,248, R. M. G. Boucher, disclose disinfecting or sterilizing medical items by contacting the item with a sporicidal composition containing 0.1 to 5 weight percent of glutaraldehyde and 0.01 to 1 weight percent of an ethoxylate type non-ionic surface active agent and at a temperature of at least 15° C. Boucher discusses this development in some detail in an article (*Amer. J. Hosp. Pharm.* 31:546–547) published June 1974.

U.S. Pat. No. 3,968,250, R. M. G. Boucher, discloses disinfecting and sanitizing fowl eggs with an aqueous solution containing 0.1 to 5% of glutaraldehyde and 0.01 to 1 percent of an ethoxylate type non-ionic surface active agent.

U.S. Pat. No. 4,093,744, M. W. Winicov et al, discloses an aqueous composition containing 2 to 4 weight percent of glutaraldehyde and 0.1 to 10 weight percent of a surfactant with a pH of 6.7 to 7.3 to kill bacterial spores. This patent further discloses "Independent analyses of the sporicidal compositions disclosed in U.S. Pat. No. 3,016,328 to Pepper et al revealed that the 10 hour contact kill time was readily obtainable when using a fresh solution, but that the efficacy of the compositions markedly decreased upon standing for prolonged periods of up to about two weeks. Further, this reduction in effectiveness was found to be attributable to the diminution of glutaraldehyde, which lost a total of about 25% of its by the end of a two week period."

*Contact Lenses* by Robert H. Hales, Williams & Wilkins Co., Baltimore, MD (1978) at page 33 records the use of glutaraldehyde as a chemical disinfectant for contact lens solution. While starting glutaraldehyde is a highly active bacterial and sporicidal agent, he notes it is toxic and irritating, unstable and requires an alkaline condition. No other mention is made of this antimicrobial agent.

SUMMARY OF THE INVENTION

In accordance with this invention, there is provided an aqueous solution for preserving and/or disinfecting contact lenses having as the active antimicrobial agent 1,5-pentandeial present in an amount from about 0.00001 to about 0.1 weight percent of said composition. Typically the solution will be an isotonic solution and optionally contains enhancing or conditioning agents.

DESCRIPTION OF THE PREFERRED EMBODIMENTS

Applicants have discovered that contact lenses can be effectively disinfected and preserved with dilute aqueous solutions of 1,5-pentanedial (popularly known as glutaraldehyde). More particularly it was found that advantageous results are obtained when the 1,5-pentanedial is present in an amount from 0.00001 to 0.1 weight percent. Preferably the 1,5-pentanedial when used without an enhancer, which is hereinafter described, the concentration is from about 0.001 to about 0.05 weight percent. When, in combination with an enhancer, the 1,5-pentanedial antimicrobial agent of this invention can be present in an amount from about 0.00001 to about 0.01 weight percent and more preferably from 0.0001 to 0.005.

The antimicrobial effect of 1,5-pentanedial can be enhanced or increased by the use of an enhancer. An enhancer can be present in an amount from zero to about 0.5 weight percent and preferably from about 0.0001 to about 0.1 weight percent. Suitable enhancers are selected from the group which includes thimerosal, phenylmercuric salts (e.g., nitrate, borate, acetate or chloride), sorbic acid, ethylenediaminetetracetic acid (EDTA) and its salts and mixtures of the foregoing enhancers. A particularly preferred enhancer is thimerosal used in an amount from 0.0001 to about 0.002 weight percent.

A typical composition of the present invention may contain, in addition to the active ingredients described earlier, buffers, cleaners, stabilizers and isotonic agents which aid in making the ophthalmic composition more comfortable to the user. These additional materials must be non-toxic and must not distort the lens.

Suitable buffers include sodium or potassium citrate, citric acid, boric acid, sodium bicarbonate and various mixed phosphate buffers including combinations of $Na_2HPO_4$, $NaH_2PO_4$ and $KH_2PO_4$. Generally, buffers may be used in amounts ranging from about 0.05 to 2.5 and preferably 0.1 to 1.5% (w/v).

Non-ionic surfactants suitable for use as cleaners include neutral polyoxyethylene fatty acid (available under the tradename Myrj 52), polysorbate 80 (tradename Tween 80) and polyethyleneglycol ether of lauryl alcohol (tradename Brij 35). These cleaners can be added in amounts ranging from 0.01 to 15 weight percent and preferably about one weight percent.

The treating solution for soft contact lenses is typically maintained at an osmotic pressure similar to that of physiologic saline, i.e., substantially isotonic, or equivalent to 0.9% saline, or with suitable agents alone or in combination to render the solution substantially isotonic. Hypotonic solution, e.g, tap water, may cause the lens to adhere tightly to the cornea while hypertonic solutions (excess saline) may result in stinging, lacrimation and a red eye.

The method of use of the solution comprises having the wearer of the soft contact lenses remove the lenses from the eyes. Then the lenses are rubbed with preserved cleaning solution, rinsed with the preserved saline solution and placed in a suitable container with a sufficient amount of the composition of the instant invention to cover the lenses. The lenses are allowed to soak preferably for period of from about 4 hours to about 12 hours at room temperature. The lenses are then removed from the solution, washed with saline solution and then replaced on the eyes.

The following examples are illustrative only and should not be construed as limiting the invention. All parts and percentages referred to herein are on a weight per volume basis. The saline solution used in the examples is an isotonic, buffered saline solution unless otherwise specified.

EXAMPLE I—Preserved Saline Solution

Isotonic saline solutions containing the indicated amounts of 1,5-pentanedial and enhancer are prepared. Each solution is exposed to approximately 1,000,000 microorganisms per ml of the indicated organism. The solution is considered effective if the concentration of *Pseudomonas aeruginosa* (ATCC No. 9027) is reduced to less than 0.1% of the initial concentration within 14 days. In this example the enhancer used is sorbic acid.

| Solution | Amount 1,5-Pentanedial (Wt. Percent) | Amount Enhancer (Wt. Percent) | Exposure Result |
|---|---|---|---|
| A | 0.0025 | — | ++ |
| B | 0.001 | — | + |
| C | 0.001 | 0.1 | ++ |
| D | 0.0005 | 0.1 | ++ |
| E | 0.0001 | 0.1 | ++ |
| F | 0.00001 | 0.1 | ++ |
| G | 0.000001 | 0.1 | + |
| H | 0.0000001 | 0.1 | + |
| I | 0.0005 | — | NE |

++ = Effective
+ = Marginal
NE = Not Effective

EXAMPLE II—Preserved Cleaner

A surfactant cleaner for lens cleaning and containing 0.1% of a neutral polyoxyethylene fatty acid non-ionic surfactant (sold under the trademark Myrj 52) by Atlas Powder Co.) is used in this comparison. To the cleaner is added the indicated amount of 1,5-pentanedial. The effectiveness against *P. aeruginosa* is determined as in Example I. The solution is considered effective against *Candida albicans* (ATCC No. 10231) if its concentration remains at or below the initial concentration of 1,000,000 microorganisms per ml for 14 days. No enhancer is added to the cleaner.

| Solution | Amount 1,5-Pentanedial (Wt. Percent) | Exposure Result (As in Example I) P. aeruginosa | C. albicans |
|---|---|---|---|
| A | 0.0025 | ++ | ++ |
| B | 0.001 | + | ++ |
| C | 0.005 | * | ++ |
| D | 0.001 | * | ++ |
| E | 0.0001 | * | ++ |
| F | 0.00001 | * | ++ |

*Not Tested

EXAMPLE III—Disinfecting Solution

Isotonic disinfecting solutions for soft contact lenses are prepared in which the antimicrobial agent is 1,5-pentanedial. Some of the solutions also contain thimerosal as an enhancing agent. The prepared solutions are exposed to approximately 1,000,000 microorganisms per ml for six hours. The solution is considered effective if there is at least a 99.9 percent reduction of the viable microorganism. The test microorganism is *Candida albicans*.

| Solution | Amount 1,5-Pentanedial (Wt. Percent) | Amount Thimerosal (Wt. Percent) | Exposure Result |
|---|---|---|---|
| A | 0.1 | — | ++ |
| B | 0.05 | — | ++ |
| C | 0.025 | — | NE |
| D | 0.005 | 0.002 | ++ |
| E | 0.001 | 0.002 | ++ |
| F | 0.0005 | 0.002 | ++ |

++ = Effective
= = Marginal
NE = Not Effective

EXAMPLE IV—Disinfecting Regimen

Two isotonic solutions, one containing 0.005 weight percent 1,5-pentanedial and the other containing 0.003 weight percent 1,5-pentanedial and 0.0002 weight percent thimerosal are evaluated in a disinfecting regimen for soft contact lenses. Both solutions are found to be effective since the regimen completely removes from the lenses or kills the six pathogenic challenge organisms recommended by the U.S. Food and Drug Administration.

The foregoing examples and methods have been described in the foregoing specification for the purpose of illustration and not limitation. Many other modifications and ramifications will naturally suggest themselves to those skilled in the art based on this disclosure. These are intended to be comprehended as within the scope of this invention.

The embodiments of the invention in which an exclusive property or privilege is claimed are defined as follows:

1. A method for preserving or disinfecting soft contact lenses comprising contacting said lenses with an aqueous solution having as the active antimicrobial agent 1,5-pentanedial present in an amount from about 0.00001 to about 0.1 weight percent of said composition, said composition being buffered for eye comfort (pH compatible) with at least one buffer in an amount from about 0.05 to 2.5 weight percent.

2. The method of claim 1 wherein the amount of 1,5-pentanedial is from about 0.001 to about 0.05 weight percent.

3. A method of disinfecting contact lenses comprising contacting the lenses for a sufficient time to disinfect the lenses with the aqueous solution of claim 1.

4. A method of inhibiting microorganism growth when sterilized contact lenses are stored in a solution comprising storing the sterilized lenses in the aqueous solution of claim 1.

* * * * *